United States Patent
Rathmacher et al.

(10) Patent No.: US 12,251,393 B2
(45) Date of Patent: Mar. 18, 2025

(54) COMPOSITIONS CONTAINING ADENOSINE TRIPHOSPHATE (ATP) AND METHODS OF USE

(71) Applicant: TSI Group Co., Ltd., Jiangyin (CN)

(72) Inventors: John Rathmacher, Story City, IA (US); Lisa Pitchford, Ames, IA (US); Shawn Baier, Polk City, IA (US); Larry Kolb, Missoula, MT (US); Naji Abumrad, Nashville, TN (US); Matthew Legge, Bannockburn (AU)

(73) Assignee: TSI Group Co., Ltd., Kiangsu Province (CN)

( * ) Notice: Subject to any disclaimer, the term of this patent is extended or adjusted under 35 U.S.C. 154(b) by 0 days.

(21) Appl. No.: 18/140,460

(22) Filed: Apr. 27, 2023

(65) Prior Publication Data

US 2023/0338408 A1 Oct. 26, 2023

Related U.S. Application Data

(63) Continuation of application No. 17/012,591, filed on Sep. 4, 2020, now Pat. No. 11,666,593.

(60) Provisional application No. 62/939,986, filed on Nov. 25, 2019, provisional application No. 62/896,335, filed on Sep. 5, 2019.

(51) Int. Cl.
| | |
|---|---|
| *A61K 31/7076* | (2006.01) |
| *A23L 33/00* | (2016.01) |
| *A23L 33/125* | (2016.01) |
| *A23L 33/15* | (2016.01) |
| *A23L 33/175* | (2016.01) |
| *A23L 33/18* | (2016.01) |

(52) U.S. Cl.
CPC ........ *A61K 31/7076* (2013.01); *A23L 33/125* (2016.08); *A23L 33/15* (2016.08); *A23L 33/175* (2016.08); *A23L 33/18* (2016.08); *A23L 33/30* (2016.08)

(58) Field of Classification Search
CPC ..... A61K 31/7076; A23L 33/18; A23L 33/30; A23L 33/175; A23L 33/125; A23L 33/15

USPC .......................................................... 514/46
See application file for complete search history.

(56) References Cited

U.S. PATENT DOCUMENTS

| | | | |
|---|---|---|---|
| 4,994,442 A | 2/1991 | Gil et al. | |
| 6,566,371 B2 | 5/2003 | Jackson | |
| 7,585,850 B2 | 9/2009 | Gorny | |
| 7,629,329 B2 * | 12/2009 | Lee | A61K 31/7076 514/47 |
| 8,703,719 B1 | 4/2014 | Abraham et al. | |
| 11,666,593 B2 * | 6/2023 | Rathmacher | A23L 33/125 514/46 |
| 2005/0261238 A1 | 11/2005 | Lee et al. | |
| 2011/0288012 A1 | 11/2011 | Somekawa et al. | |
| 2011/0305737 A1 | 12/2011 | Alexiades-Armenakas | |

OTHER PUBLICATIONS

Anonymous, "MINTEL", Database GNPG (Online); Raspberry Flavour Maximum Pre-Workout food Supplement, Jun. 7, 2018.
Anonymous, "MINTEL", Database Gnpd (Online); "Pre-Workout Boost", Sep. 7, 2018.
Lowery, Ryan P., et al., "Interaction of Beta-Hydroxy-Beta-Methylbutyrate Free Acid and Adenosine Triphosphate on Muscle Mass, Strength, and Power in Resistance Trained Individuals", Journal of Strength and Conditioning Research; vol. 30, No. 7, Jul. 1, 2016, 1843-1854.
Wikipedia, "Branched-chain amino acid", Nov. 25, 2018.
"ATP", Presentation at the conference of The Japanese Society for the Study of Xenobiotics, 2003.
"ATP 20mg [AFP]", QLifePro (instruction for package inserts of prescription drug "AFP and AFP"), Mar. 1, 2019.

* cited by examiner

*Primary Examiner* — Yih-Horng Shiao
(74) *Attorney, Agent, or Firm* — Dentons Davis Brown; Matthew W. Coryell (57) ABSTRACT

The present invention provides a composition comprising adenosine or adenosine triphosphate (ATP) acting as an absorption enhancer when combined with a nutritional material(s) such as nutrients, protein, peptides, vitamins, phytochemicals, minerals, fatty acids, or amino acids or a drug. Methods of administering ATP or adenosine to improve the bioavailability of a nutritional material(s) such as nutrients, protein, peptides, vitamins, phytochemicals, minerals, fatty acids, or amino acids or a drug are described.

17 Claims, 10 Drawing Sheets

COMPOSITIONS CONTAINING ADENOSINE TRIPHOSPHATE (ATP) AND METHODS OF USE

This application is a continuation of U.S. patent application Ser. No. 17/012,591 filed Sep. 4, 2020, which claims priority to U.S. Provisional Patent Application No. 62/939,986 filed Nov. 25, 2019, which claims priority to U.S. Provisional Patent Application No. 62/896,335 filed Sep. 5, 2019 and herein incorporates these provisional applications by reference.

BACKGROUND OF THE INVENTION

Field

The present invention relates to a composition comprising adenosine-5'-triphosphate (ATP) combined with nutrients, protein, peptides, vitamins (such as vitamin K2), amino acids, phytochemicals, minerals, fatty acids, and/or drugs, and methods of using a combination of ATP, nutrients, protein, peptides, vitamins, amino acids, phytochemicals, minerals, fatty acids, and/or drugs to enhance the bioavailability of the nutrients, protein, peptides, vitamins, amino acids, phytochemicals, minerals, fatty acids, and/or drugs. ATP acts as an absorption enhancer when administered with nutrients, protein, peptides, vitamins, amino acids, phytochemicals, minerals, fatty acids, and/or drugs.

Background

ATP

Adenosine-5'-triphosphate (ATP) has long been known as the chemical energy source for tissues including muscle. Intracellular ATP concentrations (1-10 mM) are quite high in contrast to extracellular concentrations (10-100 nM) and therefore release of ATP from cells such as erythrocytes and muscle is strictly controlled. More recently extracellular effects of ATP, acting through purinergic receptors found in most cell types, have been elicited. Several extracellular physiological functions of ATP have been described including vasodilation, reduced pain perception, and as a neurotransmission cotransmitter. Importantly, small and transient increases in vascular ATP in muscle can cause vasodilation and an increase in blood flow to the muscle. Therefore, if ATP increases blood flow to muscle, especially during periods of strenuous resistance training, substrate availability would be improved and removal of metabolic waste products would be better facilitated. Ellis et al. recently reviewed the studies supporting the role of ATP in increasing muscle blood flow through purinergic signaling and neurotransmission.

ATP has been shown to have an inotrophic effect ATP on cardiac muscle. Another study supporting systemic effects of ATP demonstrated that oral administration of ATP to rabbits for 14 days resulted in a reduction in peripheral vascular resistance, improvement of cardiac output, reduction of lung resistance, and increased arterial $PaO_2$.

Adenosine, resulting from the degradation of ATP, may also act as a signaling agent through purinergic receptors or may be degraded by adenosine deaminase. Adenosine acting through purinergic receptors can essentially mimic the effects of ATP. Adenosine infusion into muscle results in increased nitric oxide formation and similar vascular effects as seen with ATP infusion.

Fatigue resistance in repeated high intensity bouts of exercise is a much sought after attribute in athletics. This is true for both augmentation of training volume, as well as sustained force and power output in intermittent sports such as hockey. During fatiguing contractions acute adaptations in blood flow occur to stave off declines in force generating capacity. There is a tight coupling between oxygen demand in skeletal muscle and increases in blood flow. Research suggests that it is red blood cells that regulate this response by acting as "oxygen sensors". ATP is carried in red blood cells and when oxygen is low in a working muscle region, the red blood cell deforms resulting in a cascade of events which lead to ATP release and binding to endothelial cells in smooth muscle. Binding results in smooth muscle relaxation and subsequent increases in blood flow, nutrient and oxygen delivery. Specifically, extracellular ATP directly promotes the increased synthesis and release of nitric oxide (NO) and prostacyclin ($PGI_2$) within skeletal muscle and therefore directly affects tissue vasodilation and blood flow. This is supported by research suggesting increased vasodilation and blood flow in response to intra-arterial infusion and exogenous administration of ATP. These changes in blood flow likely lead to an increased substrate pool for skeletal muscle by virtue of increased glucose and $O_2$ uptake. The outcome is maintenance of energy status in the cell under fatiguing contractions.

The physiological effects of ATP have led researchers to investigate the efficacy of oral supplementation of ATP. Jordan et al. demonstrated that 225 mg per day of enteric-coated ATP supplementation for 15 days resulted in increased total bench press lifting volume (i.e. sets•repetitions•load) as well as within-group set-one repetitions to failure. More recently, Rathmacher et al. found that 15 days of 400 mg per day of ATP supplementation increased minimum peak torque in set two of a knee extensor bout. Collectively the results discussed indicate that ATP supplementation maintains performance and increases training volume under high fatiguing conditions.

Vitamin K is important for helping blood clot and preventing excessive bleeding. Evidence supports a role of Vitamin K2 (menaquinone) in various physiological processes in humans, which may impact both cardiovascular health and exercise performance. Vitamin K2 may also provide a benefit for osteoporosis and steroid-induced bone loss.

It has been unexpectedly and surprisingly discovered that ATP acts as an absorption enhancer for nutrients, protein, peptides, vitamins, amino acids, phytochemicals, minerals, fatty acids, and/or drugs. ATP increases the bioavailability of nutrients, protein, peptides, vitamins, amino acids, phytochemicals, minerals, fatty acids, and/or drugs. A need exists for a composition and methods to enhance the absorption of and/or increase the bioavailability of nutrients, protein, peptides, vitamins, amino acids, phytochemicals, minerals, fatty acids, and/or drugs.

SUMMARY OF THE INVENTION

One object of the present invention is to provide a composition for use in increasing the bioavailability of nutrients, protein, peptides, vitamins, amino acids, phytochemicals, minerals, fatty acids, and/or drugs.

A further object of the present invention is to provide a composition for use as an absorption enhancer for nutrients, protein, peptides, vitamins, amino acids, phytochemicals, minerals, fatty acids, and/or drugs.

Another object of the present invention is to provide methods of administering a composition for increasing the bioavailability of nutrients, protein, peptides, vitamins, amino acids, phytochemicals, minerals, fatty acids, and/or drugs.

These and other objects of the present invention will become apparent to those skilled in the art upon reference to the following specification, drawings, and claims.

The present invention intends to overcome the difficulties encountered heretofore. To that end, a composition comprising ATP with nutrients, protein, peptides, vitamins, amino acids, phytochemicals, minerals, fatty acids, and/or drugs is provided. The composition is administered to an animal in need thereof. All methods comprise administering to the animal an absorption enhancer such as ATP or adenosine in conjunction with nutritional materials such as nutrients, protein, peptides, vitamins, amino acids, phytochemicals, minerals, fatty acids, and/or drugs.

DETAILED DESCRIPTION OF THE INVENTION

It has been surprisingly and unexpectedly discovered that ATP acts as an absorption enhancer to increase the bioavailability of nutrients, protein, peptides, vitamins, amino acids, phytochemicals, minerals, fatty acids, and/or drugs. The present invention comprises a composition of ATP combined with nutrients, protein, peptides, vitamins, amino acids, phytochemicals, minerals, fatty acids, and/or drugs.

This combination can be used on all age groups seeking improved bioavailability of nutrients, protein, peptides, vitamins, amino acids, phytochemicals, minerals, fatty acids, and/or drugs.

In view of the above, in one embodiment the present invention provides a composition comprising an absorption enhancer, typically ATP, included with nutrients, protein, peptides, vitamins, amino acids, phytochemicals, minerals, fatty acids, and/or drugs. The inclusion of ATP with nutrients, protein, peptides, vitamins, amino acids, phytochemicals, minerals, fatty acids, and/or drugs provides elevated $C_{max}$, $T_{max}$ and/or AUC levels as compared to nutrients, protein, peptides, vitamins, amino acids, phytochemicals, minerals, fatty acids and/or drugs administered without ATP. Inclusion of ATP as an absorption enhancer with nutrients, protein, peptides, vitamins, amino acids, phytochemicals, minerals, fatty acids, and/or drugs is effective to promote the bioavailability of the nutrients, protein, peptides, amino acids, phytochemicals, minerals, fatty acids, and/or drugs. Co-administration of ATP and nutrients, protein, peptides, vitamins, amino acids, phytochemicals, minerals, fatty acids, and/or drugs causes an increase in the AUC of the nutrients, protein, peptides, vitamins, amino acids, and/or drugs as compared with administration of nutrients, protein, peptides, vitamins, amino acids, phytochemicals, minerals, fatty acids, and/or drugs without ATP. Administration of ATP with nutrients, protein, peptides, vitamins, amino acids, phytochemicals, minerals, fatty acids, and/or drugs results in an improved pharmokinetic profile as compared to administration of nutrients, protein, peptides, vitamins, amino acids, phytochemicals, minerals, fatty acids, and/or drugs without ATP.

Improved bioavailability may also improve the efficacy of the substance exhibiting improved bioavailability. Enhancing the absorption of nutrients, protein, peptides, vitamins, amino acids, and/or drugs provides improves the availability of these substances to tissues and thus provides a more rapid and efficient method to get these substances to the tissues.

As used herein, the term "bioavailability" generally means the rate and extent to which the nutrients, protein, peptides, vitamins, amino acids, phytochemicals, minerals, fatty acids, and/or drugs are absorbed and become available at the site of action. For oral dosage forms, bioavailability relates to the processes by which the active ingredient (i.e., nutrients, protein, peptides, vitamins, amino acids, phytochemicals, minerals, fatty acids, and/or drugs) is released from the oral dosage form and moves to the site of action. In general, bioavailability is the amount of nutrients, protein, peptides, vitamins, amino acids, and/or drugs systemically (i.e., blood/plasma levels) available over time.

As used herein, $T_{max}$, is the time to maximum concentration and $C_{max}$ is the observed maximum concentration. Area under the curve (AUC) refers to the mean area under the plasma concentration-time curve and is considered to be a direct measurement of the bioavailability of the nutrients, protein, peptides, vitamins, amino acids, and/or drugs.

As used herein, "absorption enhancer" shall mean any substance which is effective to increase the absorption of an agent such as nutrients, protein, peptides, vitamins, amino acids, phytochemicals, minerals, fatty acids and/or drugs through the mucosa relative to absorption without such agent.

ATP or adenosine acts as an enhancer for the absorption of macromolecules, including, nutrients, protein, peptides, vitamins, amino acids, phytochemicals, minerals, fatty acids, and/or drugs into the body. Adenine nucleotides or adenosine and inorganic phosphate are including the scope of this invention, including adenosine 5'-monophosphate, adenosine 5'-diphosphate, adenosine 5'-triphosphate and mixtures thereof, pharmaceutically acceptable salts thereof or chelate thereof, or metal complex thereof or liposome thereof.

Adenosine-5'-triphosphate (ATP)

Oral administration of ATP is usually in the form of Adenosine-5'-Triphospate Disodium. In the present invention, Adenosine-5'-Triphosphate Disodium or any form of ATP or adenosine suitable for oral administration may be combined with any of the known coatings suitable for imparting enteric properties in granular form.

One of skill in the art recognizes that ATP may be incorporated into the delivery and/or administration form in a fashion so as to result in a typical dosage range of about 10 mg to about 80 grams, though more or less may be desirable depending on the application and other ingredients.

The composition of ATP and nutrients, protein, peptides, vitamins, amino acids, and/or drugs is administered to an animal in any suitable manner. Acceptable forms include, but are not limited to, solids, such as tablets or capsules, and liquids, such as enteral solutions. Also, the composition can be administered utilizing any pharmaceutically acceptable carrier. Pharmaceutically acceptable carriers are well known in the art and examples of such carriers include various starches and saline solutions. In the preferred embodiment, the composition is administered in an edible form. In addition, an effective dosage range may be administered in divided dosages, such as two to three times per day.

The present invention can be used with enteral feeding tubes that deliver nutrients and medications. Such feeding tubes may be used to deliver nutrients and medications to the stomach, small bowel, and jejunal regions. Feeding tubes may be nasoenteric, inserted through the mouth, or percutaneous. Enteral feeding may be administered by various methods, including continuous, cyclic, bolus and intermittent.

The present invention can be used with oral nutritional products containing nutrients, protein, peptides, vitamins, and/or amino acids, such as Ensure, IsoPure, Boost, Glucerna, Jevity, Osmolite or other supplemental nutritional liquids.

ATP is present in the composition in any form. A range of ATP in the present invention includes ATP in the amount of around 10 milligrams to around 80 grams. In the preferred embodiment, the range of ATP is around 100 milligrams to around 1.6 grams.

When the composition is administered orally in an edible form, the composition is preferably in the form of a dietary supplement, foodstuff or pharmaceutical medium, more preferably in the form of a dietary supplement or foodstuff. Any suitable dietary supplement or foodstuff comprising the composition can be utilized within the context of the present invention. One of ordinary skill in the art will understand that the composition, regardless of the form (such as a dietary supplement, foodstuff or a pharmaceutical medium), may include amino acids, proteins, peptides, carbohydrates, fats, sugars, vitamins, phytochemicals, minerals and/or trace elements.

In order to prepare the composition as a dietary supplement or foodstuff, the composition will normally be combined or mixed in such a way that the composition is substantially uniformly distributed in the dietary supplement or foodstuff. Alternatively, the composition can be dissolved in a liquid, such as water, or emulsified in a liquid.

The composition of the dietary supplement may be a powder, a gel, a liquid or may be tabulated or encapsulated.

Although any suitable pharmaceutical medium comprising the composition can be utilized within the context of the present invention, preferably, the composition is combined with a suitable pharmaceutical carrier, such as dextrose or sucrose.

Methods of calculating the frequency by which the composition is administered are well-known in the art and any suitable frequency of administration can be used within the context of the present invention (e.g., one 6 g dose per day or two 3 g doses per day) and over any suitable time period (e.g., a single dose can be administered over a five minute time period or over a one hour time period, or, alternatively, multiple doses can be administered over an extended time period). The combination of ATP and nutritional materials (including nutrients, protein, peptides, vitamins, phytochemicals, minerals, fatty acids, and amino acids) and/or drugs can be administered over an extended period of time, such as weeks, months or years.

It will be understood by one of ordinary skill in the art that ATP and nutrients, protein, peptides, vitamins, amino acids, and/or drugs do not have to be administered in the same composition to perform the claimed methods. Stated another way, separate capsules, pills, mixtures, liquids etc. of ATP and nutrients, protein, peptides, vitamins, amino acids, phytochemicals, minerals, fatty acids, and/or drugs may be administered to a subject to carry out the claimed methods.

Any suitable dose of ATP can be used within the context of the present invention.

Methods of calculating proper doses are well known in the art.

EXPERIMENTAL EXAMPLES

The following examples will illustrate the invention in further detail. It will be readily understood that the composition of the present invention, as generally described and illustrated in the Examples herein, could be synthesized in a variety of formulations and dosage forms. Thus, the following more detailed description of the presently preferred embodiments of the methods, formulations and compositions of the present invention are not intended to limit the scope of the invention, as claimed, but it is merely representative of the presently preferred embodiments of the invention.

Example 1

The purpose of this study was to determine whether oral ATP supplementation would affect the absorption of nutrients from the gastrointestinal (GI) tract following consumption of a mixed protein shake.

Methods

Six young, healthy adults (3 M, 3 F) participated in this study. All were free from GI disease/symptoms and were not taking any medication or supplements known to alter GI function or nutrient absorption.

The study utilized a placebo-controlled, cross-over study design with a balanced treatment order. Trials were separated by 7 days.

Subjects arrived to the laboratory in the morning following an overnight fast. A polyethylene catheter was inserted and a baseline blood sample is drawn.

Participants consumed either 400 mg ATP or a placebo capsule with 4 oz of water.

Ten minutes after consuming the supplement capsule, participants consumed a 10-oz vegan protein shake containing 20 g protein, 1.5 g HMB, and 5 g sucrose.

Blood samples were taken at 15, 30, 45, 60, 75, 90, 120, 150, and 180 minutes after shake ingestion.

Plasma was separated and frozen for analysis of amino acids levels.

Results

Figure 1:
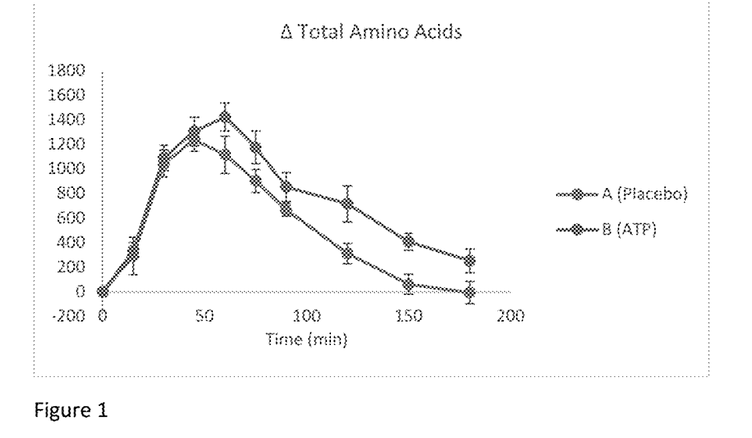
FIG. 1 is a graph showing the absorption of total amino acids

In FIG. 1 depicting total amino acids, ATP increased $C_{max}$ (5%) and AUC (7%). Based on unadjusted t-tests, the change in total amino acids (ΔTAA) is higher with ATP supplementation at all timepoints.

Figure 2:
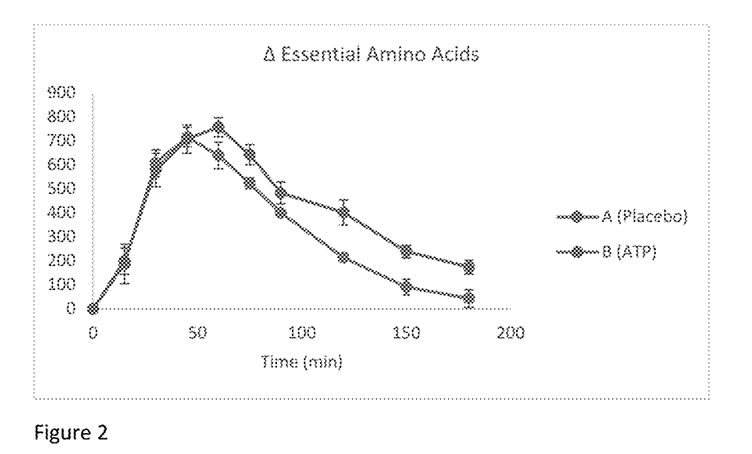
FIG. 2 is a graph showing the absorption of essential amino acids.

In FIG. 2 depicting essential amino acids, based on unadjusted t-tests, the change in essential amino acids (ΔEAA) is higher at timepoints between 60 and 180 minutes with ATP supplementation.

Figure 3:
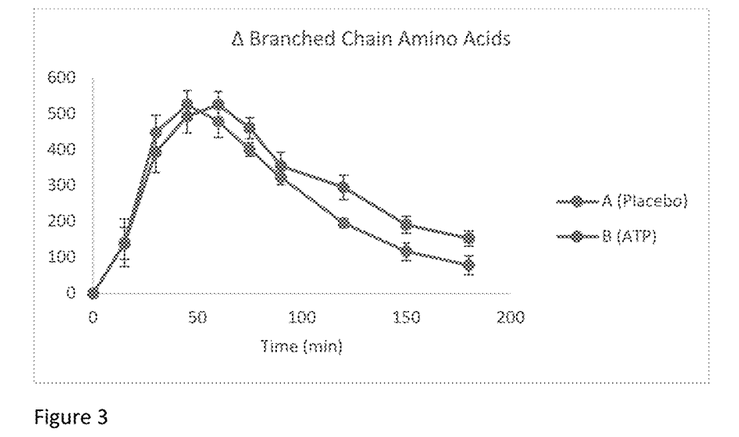
FIG. 3 is a graph showing the absorption of branched chain amino acids
Figure 4:
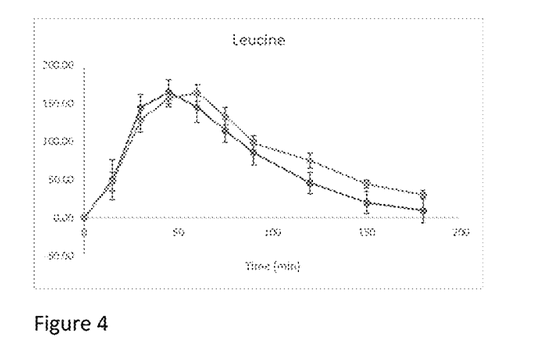
FIG. 4 is a graph showing the absorption of leucine.
Figure 5:
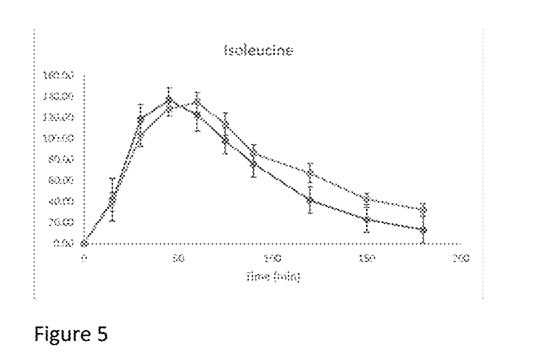
FIG. 5 is a graph showing the absorption of isoleucine.
Figure 6:
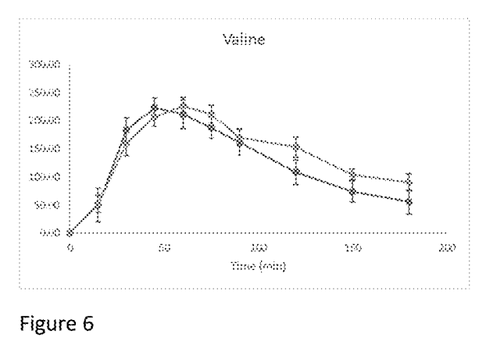
FIG. 6 is a graph showing the absorption of valine.
Figure 7:
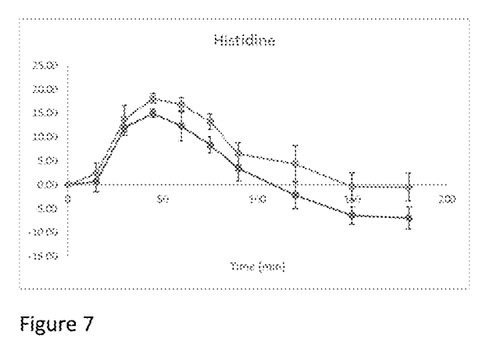
FIG. 7 is a graph showing the absorption of histidine.
Figure 8:
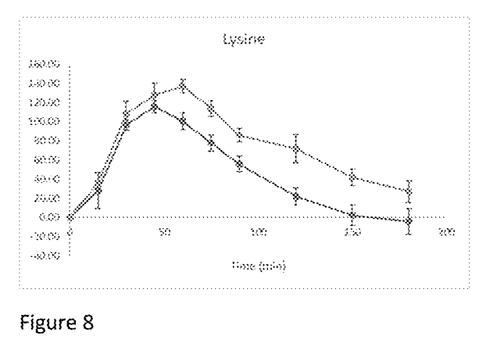
FIG. 8 is a graph showing the absorption of lysine.
Figure 9:
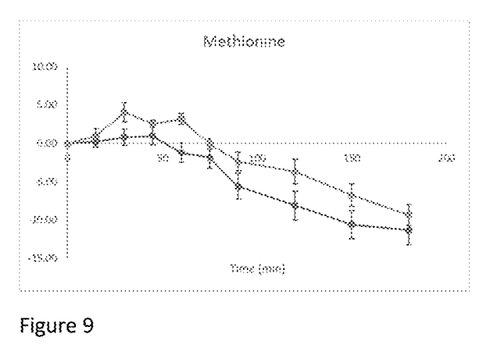
FIG. 9 is a graph showing the absorption of methionine.
Figure 10:
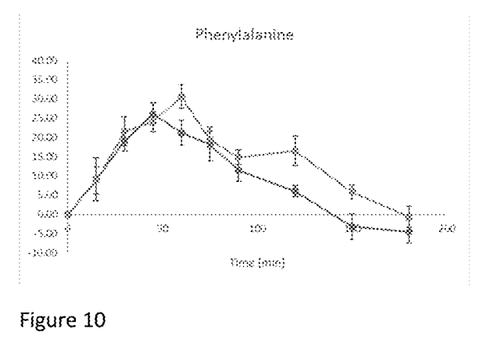
FIG. 10 is a graph showing the absorption of phenylalanine.
Figure 11:
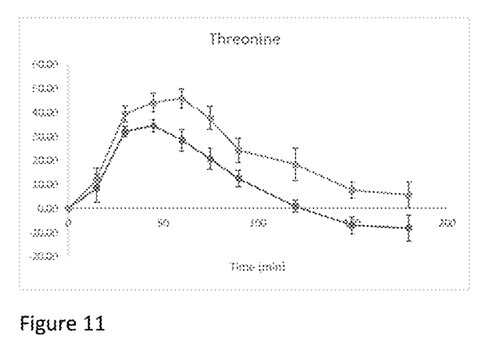
FIG. 11 is a graph showing the absorption of threonine.
Figure 12:
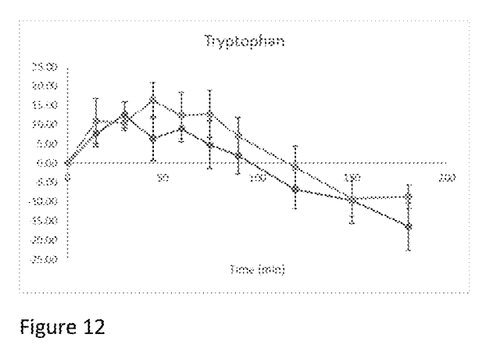
FIG. 12 is a graph showing the absorption of tryptophan.

In FIG. 3 depicting branched chain amino acids, based on unadjusted t-tests, the change in branched chain amino acids (ΔBCAA) is higher with ATP supplementation at 120 minutes.

For the AUC for individual amino acids, ATP increased AUC for

Figure 13:
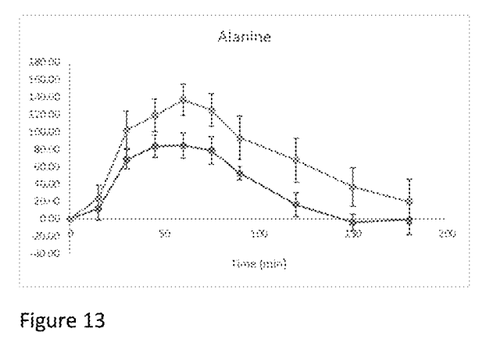
FIG. 13 is a graph showing the absorption of alanine.
Figure 14:
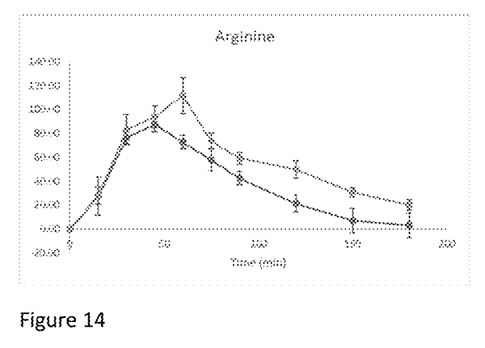
FIG. 14 is a graph showing the absorption of arginine.
Figure 15:
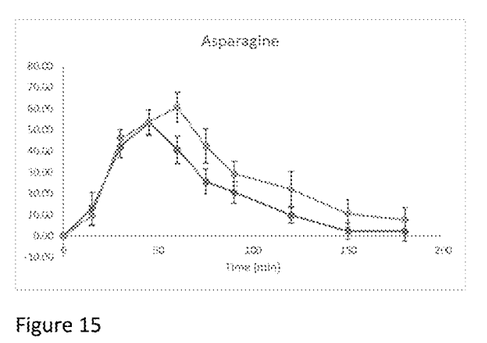
FIG. 15 is a graph showing the absorption of asparagine.
Figure 16:
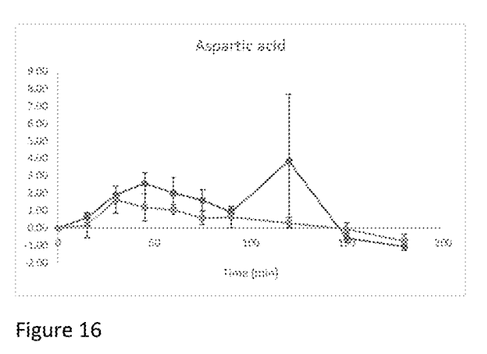
FIG. 16 is a graph showing the absorption of aspartic acid.
Figure 17:
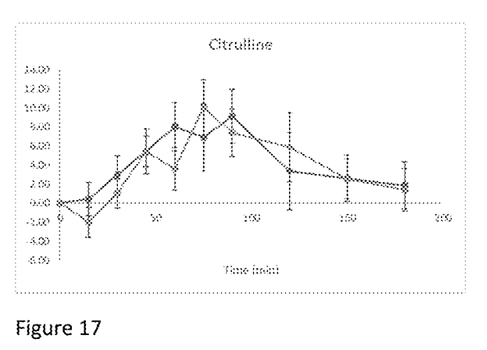
FIG. 17 is a graph showing the absorption of citrulline.
Figure 18:
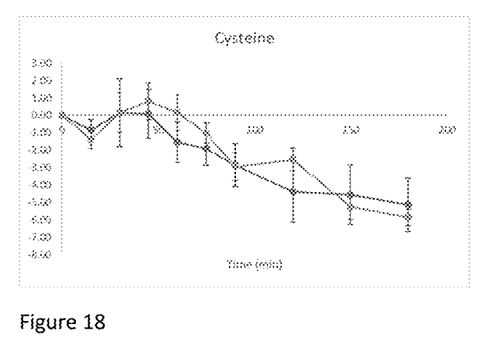
FIG. 18 is a graph showing the absorption of cysteine.
Figure 19:
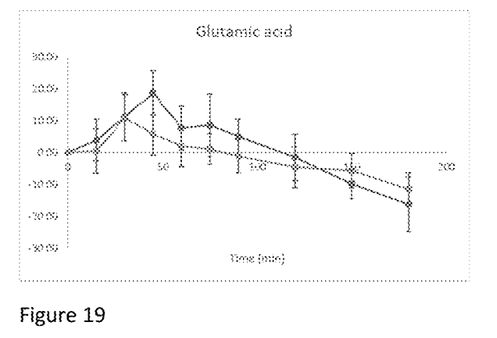
FIG. 19 is a graph showing the absorption of glutamic acid.
Figure 20:
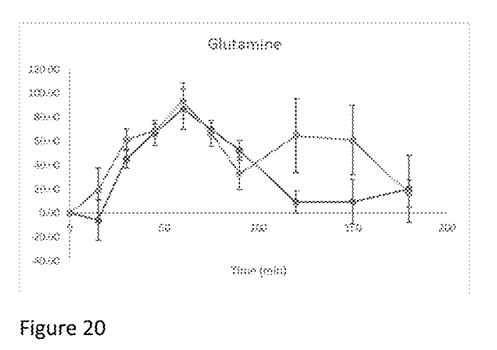
FIG. 20 is a graph showing the absorption of glutamine.
Figure 21:
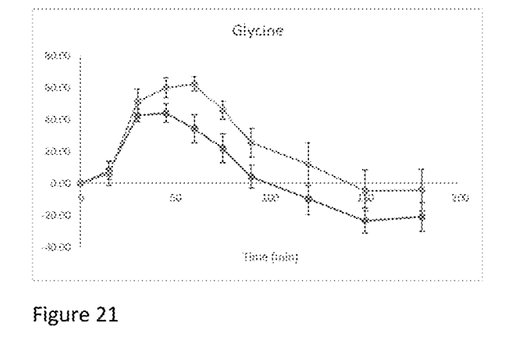
FIG. 21 is a graph showing the absorption of glycine.
Figure 22:
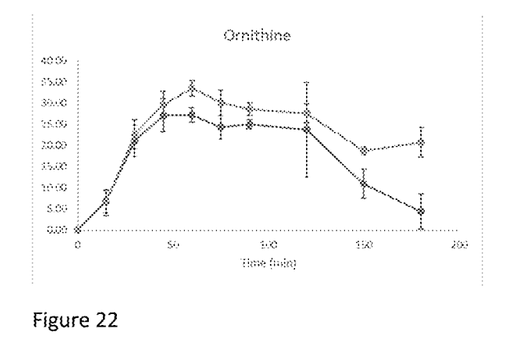
FIG. 22 is a graph showing the absorption of ornithine.
Figure 23:
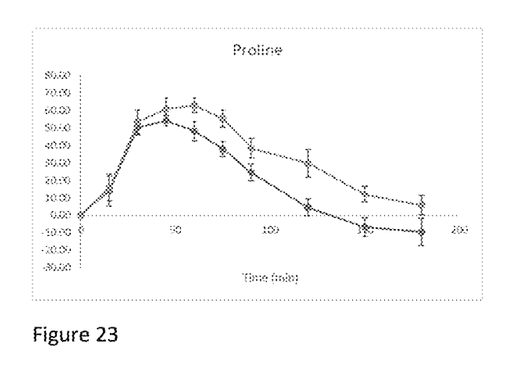
FIG. 23 is a graph showing the absorption of proline.
Figure 24:
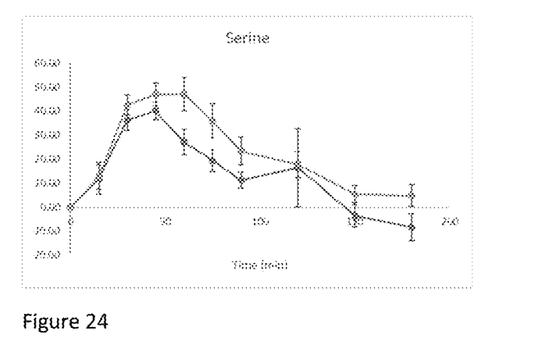
FIG. 24 is a graph showing the absorption of serine.
Figure 25:
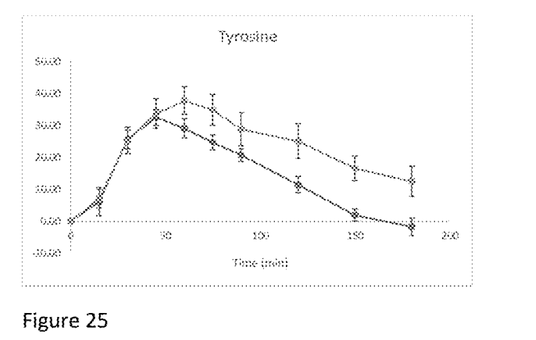
FIG. 25 is a graph showing the absorption of tyrosine.

Glutamine (10%, p=0.02) (FIG. 20)
Citrulline (13%; p=0.06) (FIG. 17)
Asparagine (20%; p=0.04) (FIG. 15)
Alanine (19%; p=0.07) (FIG. 13)

Individual Amino Acids

Plots of each individual amino acid are depicted in FIGS. 4 through 25. These are expressed as change from baseline (Blue=Placebo, Orange=ATP).

ATP increases total amino acid availability during 3 hours post-prandial to a mixed protein shake. The individual amino acids that demonstrated increased bioavailability include glutamine, asparagine, alanine and citrulline. Without being limited by any particular theory, this may occur due to ATP enhancing uptake of select amino acids from the gut and/or inhibiting the clearance of select amino acids from circulation. ATP may affect the glutamine transporters in the enterocytes causing increased absorption of glutamine, asparagine, alanine and citrulline.

The data demonstrates that ATP acts as an absorption enhancer for certain amino acids, including glutamine, asparagine, arginine, alanine and citrulline. The addition of ATP to any composition administered for the benefits of these amino acids will improve the bioavailabilty of these amino acids. For example, U.S. Pat. No. 6,031,000 describes administering β-hydroxy-β-methylbutyric acid (UMB) with at least one amino acid, including glutamine, for treating disease-associated wasting (including age associated muscle wasting), decreasing serum-level triglycerides, decreasing the serum viral load, and redistributing fat. Addition of ATP to the compositions and methods of use of the compositions of this patent improves the bioavailability of the amino acids in the compositions. Juven is a product used for wound healing and to build and maintain lean body mass that contains glutamine, arginine and HMB. Addition of ATP to this type of amino-acid containing product improves the bioavailability of the amino acids in these products.

Glutamine has been shown to be used in instances of metabolic stress, impaired gastrointestinal function due to severe trauma, diarrhea, inflammatory bowel disease, and surgery, severe burns or injury due to chemotherapy or radiation, instances of malabsorptive conditions (such as Crohn's disease), acute trauma and wound healing. Addition of an absorption enhancer such as ATP to a composition containing glutamine results in the improved bioavailability of glutamine and improved systemic utilization of glutamine Arginine has been shown to be useful for treating or lessening the effects of pulmonary hypertension in sickle cell disease, wound healing, improving kidney function, maintaining immune and hormone function, dilating and relaxing the arteries, improving blood flow in the arteries of the heart, improving symptoms of clogged arteries, chest pain and coronary artery disease, improving erectile dysfunction, decreasing blood pressure and improving hypertension. Addition of an absorption enhancer such as ATP to a composition containing arginine results in the improved bioavailability of glutamine and improved systemic utilization of arginine.

Example 2

The purpose of this study was to assess the effects of ATP and K2 supplementation individually and in combination.

Methods

A total of 11 subjects (6 male, 5 female; ages 20-30) completed all study periods. Treatments were administered in a double-blinded, crossover design with a Latin Square sequence design to minimize confounding effects of treatment order. Participants were semi-randomly assigned to treatment sequences; at least one male and one female participant were assigned to each sequence to minimize any confounding effects of sex.

During each study period, participants consumed one of 4 supplements for 15 days:

ATP (400 mg/d)
K2 (200 μg/d) as menaquinone-7 (NOW® MK-7, containing MenaQ7®)
ATP (400 mg/d)+K2 (200 μg/d)
placebo Blood samples were taken before and after each supplementation period for the measurement of serum K2 concentration, carboxylated/undercarboxylated osteocalcin ratio (a marker of K2 function), and clinical chemistry and hematology.

Results

Participant Characteristics

|  | Mean | SE |
| --- | --- | --- |
| Sex (M/F) | 6/5 |  |
| Age (y) | 22.8 | 1.1 |
| Height (cm) | 173.6 | 2.6 |
| Weight (kg) | 68.3 | 3.0 |
| Body Fat (%) | 16.8 | 1.5 |
| BMI (kg/m$^2$) | 22.6 | 0.8 |

Supplement compliance was 94±2%. All participants consumed ≥73% of the provided doses for all periods.

Blood samples were analyzed for K2 levels. Average serum K2 levels were 1.08±0.25 ng/mL after 15 days of K2 supplementation and 2.29±0.49 ng/mL after 15 days of K2+ATP supplementation (p<0.05). Two participants did not accumulate K2 in serum during either of the treatment periods. Consuming ATP and K2 together enhances the bioavailability of K2.

For safety analyses, blood samples were also analyzed for clinical chemistry and hematology. Though some small differences were observed, all were small and none were clinically relevant. No adverse effects were observed for any of the supplements.

Figure 26:
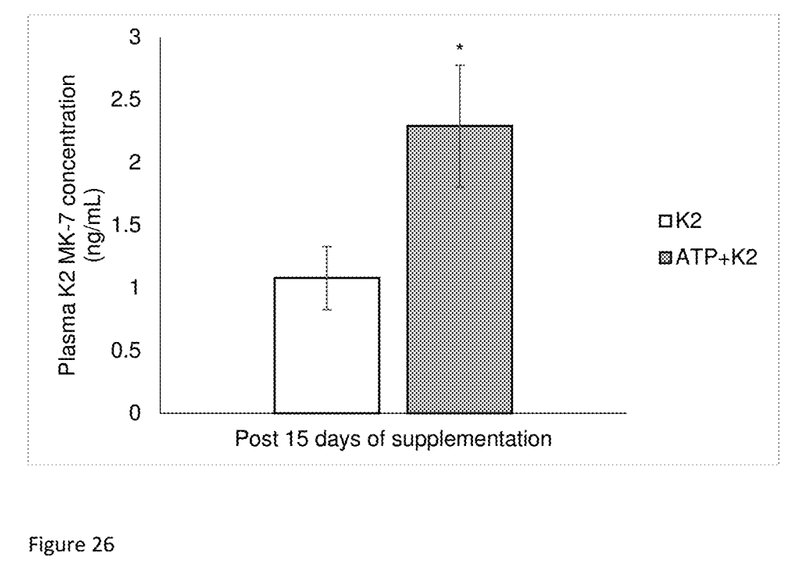
FIG. 26 shows the plasma K2 concentration with and without ATP.
Figure 27:
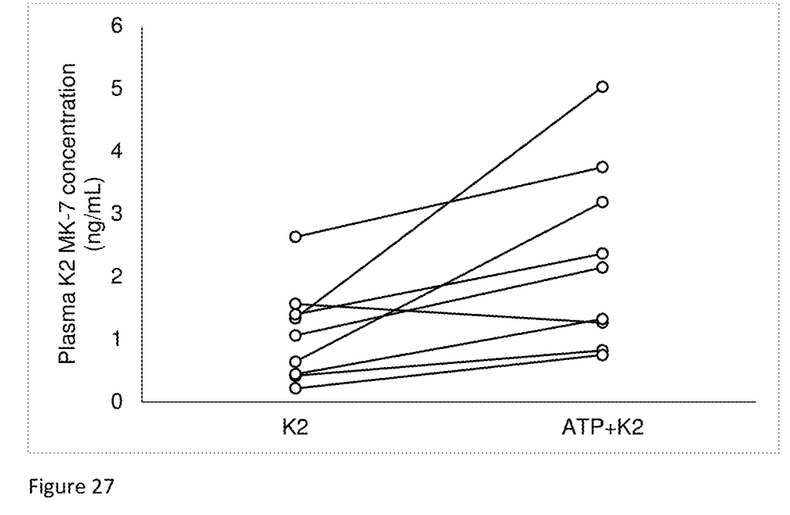
FIG. 27 shows the plasma K2 concentration with and without ATP.

In FIGS. 26-27, post-supplementation values are presented. In FIG. 26, plasma levels of Vitamin K2 as menaquinone-7 ($K_2$ MK-7) were measured by LC/MS/MS before and after 15 days of supplementation with 200 μg/d $K_2$ MK-7 with or without 400 mg/d ATP (n=9). After 15 days of supplementation, mean plasma $K_2$ MK-7 levels were 113% higher after ATP+K2 supplementation vs. K$_2$ supplementation alone. Data presented as mean+SE*Statistically significant difference (p<0.05) between K2 and ATP+K2.

In FIG. 27, plasma levels of Vitamin K2 as menaquinone-7 (K$_2$ MK-7) were measured by LC/MS/MS before and after 15 days of supplementation with 200 µg/d K$_2$ MK-7 with or without 400 mg/d ATP (n=9, lines represent individual subjects). After 15 days of supplementation, plasma levels of Vitamin K$_2$ as menaquinone-7 (K$_2$ MK-7) were higher in 8/9 subjects after ATP+K2 supplementation vs. K$_2$ supplementation alone.

The combination of ATP+Vitamin K2 improves the bioavailability of K2, as average vitamin K2 levels were nearly twice as high when vitamin K2 supplements were consumed along with 400 mg/d ATP compared to when vitamin K2 supplements were consumed with placebo capsules.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention. The terms subject and animal are used interchangeably throughout this application and are in no way limited to one term or the other.

The invention claimed is:

1. A method for increasing the bioavailability of a nutritional material in an animal comprising:
   administering to the animal:
      at least one nutritional material;
      an effective amount of β-hydroxy-β-methylbutyric acid (HMB) as an additional nutritional material; and
      an absorption enhancer,
   wherein the absorption enhancer that increases absorption of the at least one nutritional material is adenosine triphosphate (ATP) or adenosine.

2. The method of claim 1, wherein the nutritional material is nutrients, proteins, peptides, vitamins, or amino acids.

3. A method for improving the absorption of a nutritional material in a human, comprising:
   administering to the human:
      an absorption enhancer that increases absorption of at least one nutritional material;
      the at least one nutritional material; and
      an effective amount of β-hydroxy-β-methylbutyric acid (HMB) as an additional nutritional material,
   wherein the absorption enhancer is adenosine triphosphate (ATP) or adenosine.

4. The method of claim 3, wherein the nutritional material is nutrients, proteins, peptides, vitamins, or amino acids.

5. The method of claim 4, wherein the nutritional material is amino acids.

6. The method of claim 5, wherein the amino acids are essential amino acids.

7. The method of claim 5, wherein the amino acids are branched chain amino acids.

8. The method of claim 1, wherein absorption enhancer is administered in a dose in the range of about 10 milligrams to about 80 grams.

9. The method of claim 1, wherein absorption enhancer is administered in a dose in the range of about 100 milligrams to about 1.6 grams.

10. The method of claim 1, wherein the administration is performed to administer a single dose.

11. The method of claim 1, wherein the administration is divided to administer multiple doses over time.

12. The method of claim 4, wherein the nutritional material is a vitamin.

13. The method of claim 1, wherein the at least one nutritional material, the effective amount of HMB, and the absorption enhancer are administered as a dietary supplement.

14. The method of claim 1, wherein the at least one nutritional material, the effective amount of HMB, and the absorption enhancer are administered as a foodstuff.

15. The method of claim 3, wherein the absorption enhancer is administered in a dose in the range of about 10 milligrams to about 80 grams.

16. The method of claim 3, wherein the absorption enhancer is administered in a dose in the range of about 100 milligrams to about 1.6 grams.

17. The method of claim 3, wherein the administration is performed to administer a single dose.

* * * * *